US009161685B2

United States Patent
Shimada

(10) Patent No.: US 9,161,685 B2
(45) Date of Patent: Oct. 20, 2015

(54) PERIMETER

(75) Inventor: Satoshi Shimada, Shizuoka (JP)

(73) Assignee: KOWA COMPANY, LTD., Aichi (JP)

(*) Notice: Subject to any disclaimer, the term of this patent is extended or adjusted under 35 U.S.C. 154(b) by 209 days.

(21) Appl. No.: 14/110,824

(22) PCT Filed: Apr. 12, 2012

(86) PCT No.: PCT/JP2012/059997
§ 371 (c)(1),
(2), (4) Date: Oct. 9, 2013

(87) PCT Pub. No.: WO2012/141240
PCT Pub. Date: Oct. 8, 2012

(65) Prior Publication Data
US 2014/0036231 A1 Feb. 6, 2014

(30) Foreign Application Priority Data
Apr. 13, 2011 (JP) ................................. 2011-088894

(51) Int. Cl.
*A61B 3/02* (2006.01)
*A61B 3/00* (2006.01)
*A61B 3/024* (2006.01)

(52) U.S. Cl.
CPC ............... *A61B 3/0025* (2013.01); *A61B 3/024* (2013.01)

(58) Field of Classification Search
USPC ................... 351/200, 203, 205–246
See application file for complete search history.

(56) References Cited

U.S. PATENT DOCUMENTS

2008/0036966 A1* 2/2008 Shimada ........................ 351/224
2014/0049751 A1* 2/2014 Oouchi et al. ................ 351/221

FOREIGN PATENT DOCUMENTS

| JP | 2004-122236 | 4/1992 |
| JP | 2007-195787 | 8/2007 |
| JP | 2009-034480 | 2/2009 |
| JP | 2009-136424 | 6/2009 |
| JP | 2010-246779 | 11/2010 |
| JP | 2010-282336 | 12/2010 |

OTHER PUBLICATIONS

International Search Report mailed on May 22, 2012, issued by Japanese Patent Office, pp. 1-3 (and English translation) in Int'l App. PCT/JP2012/059997.

* cited by examiner

*Primary Examiner* — Joseph P Martinez
*Assistant Examiner* — Brandi Thomas
(74) *Attorney, Agent, or Firm* — Duane Morris LLP

(57) ABSTRACT

The perimeter (2), which has a perimetry means (13) that measures the visual field of a test eye and outputs the results thereof as measurement results (MR), is configured by comprising: a measurement database memory (17) wherein multiple measurement results of previous visual field measurements are stored as a measurement database (MDB) in a form that is divided into a database (DB1) pertaining to normal eyes and a database (DB2) pertaining to eyes with glaucoma; a means (16) for assessing whether or not the measurement results (MR) for the test eye can be used as measurement results for normal eyes; and a means (15) that, when it is determined that the measurement results can be used as measurement results for normal eyes, adds the measurement results to the database (DB1) pertaining to normal eyes along with database search attribute data (data such as the subject's age, sex, race, visual acuity, refractive index, diagnosis, residence, date and time of examination, etc.).

13 Claims, 3 Drawing Sheets

PERIMETER

CROSS REFERENCE TO RELATED PATENT APPLICATIONS

The present application is a U.S. national stage application under 35 U.S.C. §371 of PCT Application No. PCT/JP2012/059997, filed Apr. 12, 2012, which claims priority to JP2011-088894 filed on Apr. 13, 2011, the entireties of which are incorporated by reference herein.

TECHNICAL FIELD

This invention relates to a perimeter that can store measurement results of a visual field as a database.

BACKGROUND ART

A device as shown in a blow-mentioned patent related document 1 is known as one of devices that store measurement results of an ophthalmology apparatus, such as a perimeter, a tonometer and an optometry apparatus, as a database.

PRIOR ART

Patent Related Document

Patent related document 1: Japanese patent application publication No. 2000-300517

DISCLOSURE OF INVENTION

Problems to be Solved by Invention

However, a device as shown in the patent related document 1 simply collects the measurement data every each test eye (patient), and does not statistically collect states of the visual fields according to the condition of the test eye, such as normal eyes and eyes with glaucoma, based upon the measurement results of many test eyes. Then, it was not possible to evaluate the measurement results using these databases and judge the condition of the test eye.

The object of the invention is to provide a perimeter having the database that collects the results of the visual field measurement of the test eyes according to the condition (including normal eyes) therein or in a proper external database unit through a communication line, such as the Internet, the perimeter being usable for diagnosis of the test eyes.

Means for Solving Problems

A first aspect of the invention is a perimeter (2) having perimetry means (13) that measures a visual field of a test eye and outputs its results as measurement results (MR), comprising:

a measurement database memory (17) that stores the measurement results regarding normal eyes from two or more measurement results of previous visual field measurements as a database regarding normal eyes (DB1);

normal eyes data judging means (16) that judges as to whether the measurement results (MR) of the test eye is usable as the measurement results of normal eyes; and database control means (15) that when the normal eyes data judging means judged the measurement results to be usable as the measurement results of normal eyes, adds the measurement results to the database regarding normal eyes (DB1) together with attribution data for searching database (for example, data such as the subject's age, sex, race, visual acuity, refractive index, diagnosis, residence, date and time of examination).

The perimeter according to the invention may be configured in such a way that a computer function is incorporated into the main body of the perimeter or the measurement unit of the perimeter and a commercial personal computer are connected with each other.

A second aspect of the invention is the perimeter, wherein the measurement database memory (17) stores the database regarding eyes with glaucoma in addition to the database regarding normal eyes, and stores two or more measurement results of previous visual field measurements as a measurement database (MDB), differentiating the database regarding normal eyes (DB1) and the database regarding eyes with glaucoma (DB2) from each other.

A third aspect of the invention is the perimeter, further comprising a sensitivity distribution memory that stores sensitivity distribution data (DA1) showing sensitivity distribution of the test eyes of each measurement point in the visual filed measurement on the normal eyes, wherein the normal eyes data judging means (16) judges as to whether the measurement results is usable as the measurement results of normal eyes by such a judgment as to whether the measurement results is included in the middle sensitivity region of the sensitivity distribution data (DA1) between the lowest sensitivity region and the highest sensitivity region, and when it is included in the middle sensitivity region, the measurement results is judged to be usable as one of normal eyes.

A fourth aspect of the invention is the perimeter, further comprising a model memory that stores visual angle-sensitivity distribution model (DA2) showing a sensitivity distribution in normal eyes with respect to the visual angle, wherein the normal eyes data judging means (16) judges as to whether the measurement results is usable as the measurement results of normal eyes by a judgment as to whether a divergence degree of the measurement results with respect to the visual angle-sensitivity distribution model is a predetermined value or lower, and judges the measurement results to be usable as the measurement results of normal eyes when such a divergence degree is a predetermined value or lower.

A fifth aspect of the invention is the perimeter, further comprising sensitivity distribution computing means (16) that reads the database regarding normal eyes (DB1) out of the measurement database memory (17), computes sensitivity distribution data (DA1) that shows the distribution of the sensitivity of the test eyes of each measurement point, and stores the computed in the sensitivity distribution memory.

A sixth aspect of the invention is the perimeter, further comprising distribution model computing means (16) that reads the database regarding normal eyes (DB1) out of the measurement database memory (17) so as to compute the visual angle-sensitivity distribution model (DA2), and stores the computed in the model memory.

A seventh aspect of the invention is the perimeter, further comprising a sensitivity distribution memory that stores sensitivity distribution data (DA1) showing a sensitivity distribution of the test eyes of each measurement point in the visual field measurement on the normal eyes, and a model memory that stores a visual angle-sensitivity distribution model showing the sensitivity distribution in the normal eyes with respect to the visual angle, wherein the normal eyes data judging means (16) judges as to whether the measurement results is usable as the measurement results of normal eyes by 1) a judgment as to whether the measurement results is included in a middle sensitivity region of the sensitivity distribution data (DA1) between a lowest sensitivity region and a highest sensitivity region and 2) a judgment as to whether a divergence degree of the measurement results with respect to the visual angle-sensitivity distribution model (DA2) is a predetermined value or lower, and judges the measurement results to be usable as the measurement results of normal eyes when the measurement results is included in the middle sensitivity region and the divergence degree of the measurement results with respect to the visual angle-sensitivity distribution model is a predetermined value or lower.

A eighth aspect of the invention is the perimeter, further comprising sensitivity distribution computing means that reads the database regarding normal eyes out of the measurement database memory so as to compute sensitivity distribution data showing the distribution of the sensitivity of the test eyes of each measurement point, and stores the computed in the sensitivity distribution memory, and distribution model computing means that reads the database regarding normal eyes out of the measurement database memory so as to compute the visual angle-sensitivity distribution model, and stores the computed in the model memory.

A ninth aspect of the invention is the perimeter, further comprising judgment result output means (19) that displays the measurement results on a display (20) when the normal eyes data judging means (16) judged the measurement results to be unusable as the measurement results of normal eyes, wherein the database managing means (15) adds the measurement results to the database regarding eyes with glaucoma (DB2) together with the attribution data for searching database when a signal that shows the measurement results (MR) is glaucoma is inputted.

A tenth aspect of the invention is a perimeter having perimetry means that measures a visual field of a test eye and outputs its results as measurement results, comprising:

a data storing means that stores the measurement results regarding normal eyes from two or more measurement results of previous visual field measurements in a measurement database memory provided at an outside of the perimeter as a database regarding normal eyes;

normal eyes data judging means that judges as to whether the measurement results of the test eye is usable as the measurement results of normal eyes; and database control means that when the normal eyes data judging means judged the measurement results to be usable as the measurement results of normal eyes, adds the measurement results to the database regarding normal eyes together with attribution data for searching database.

An eleventh aspect of the invention is the perimeter, wherein the database regarding normal eyes is stored in the measurement database memory, divided into 1) a default database and 2) a storage database, and 1) the default database storing the two or more measurement results of the test eyes that are considered to be normal eyes in the measurement database memory in advance as a database before the perimeter is actually used for the measurement of the test eye, and 2) the storage database storing multiple measurement results of the normal eyes measured with the perimeter by adding the measurement results measured by the perimeter to the default database in order.

A twelfth aspect of the invention is the perimeter, further comprising database producing means that searches and extracts the measurement results out of the default database and the storage database with the attribution data for searching the database as a parameter so as to produce and construct a new database.

Effects of Invention

According to the first and the second aspects of the invention, the normal eyes data judging means (16) judges as to whether the measurement results is usable as the measurement results of normal eyes every each measurement of the visual field of the test eye, and the database managing means (15) adds the measurement results to the database regarding the normal eyes (DB1) together with the attribution data for searching the database (such as the subject's age, sex, race, visual acuity, refractive index, diagnosis, residence, date and time of examination) when the measurement results was judged to be usable as the measurement results of the normal eyes, so that it is possible to selectively collect the results of the visual field measurement of the normal eyes as the database and to properly use such a database at the time of the later diagnosis of the test eye.

When the measurement results was judged to be unusable as the measurement results of normal eyes, the measurement results is displayed on the display (20), and when a signal showing the measurement results (MR) is the glaucoma is inputted through the input means, the measurement results is added to the database (DB2) regarding eyes with glaucoma together with the attribution data for searching the database as shown in the ninth aspect of the invention, so that it is possible to selectively collect the measurement results of the visual field measurement of the eyes with the glaucoma also as the database and to properly use such a database at the time of the later diagnosis of the test eye.

According to the third and the fourth aspects of the invention, as to whether the measurement results is usable as the measurement results of normal eyes is judged based upon the sensitivity distribution data (DA1) showing the sensitivity distribution of the test eye of each measurement point or the visual angle-sensitivity distribution model (DA2), so that it is possible to automatically judge the measurement results from statistical or physiological aspect so as to improve the accuracy of the judgment.

According to the fifth and the sixth aspects of the invention, the sensitivity distribution data (DA1) or the visual angle-sensitivity distribution model (DA2) is computed based upon the database regarding normal eyes (DB1) stored in the perimeter, so that it is possible to reflect the previous measurement data in the perimeter on the database and to reflect the local characteristics in the place where the perimeter is located on the database.

The number in parentheses shows the corresponding element in the drawings for the sake of convenience, accordingly, the descriptions are not restricted and bound by the descriptions on the drawings.

PREFERRED EMBODIMENT

An embodiment of the invention is now explained, referring to appended drawings.

Figure 1:
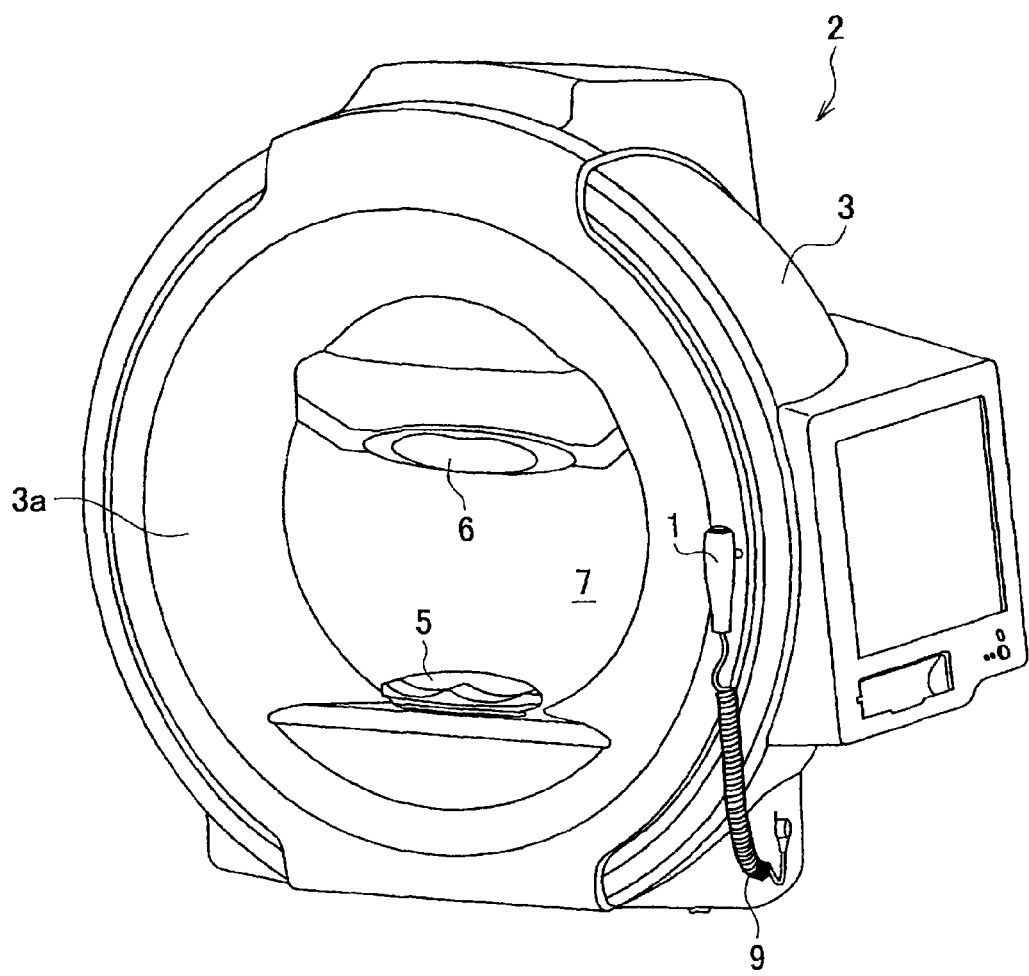
FIG. 1 is a perspective view that shows an instance of a perimeter to which the invention is applied.

As shown in FIG. 1, a perimeter 2 has a main body 3 the whole of which is in the shape of a box, and a jaw stand 5 and a forehead pad 6 are provided at a front face 3a of the main body 3. A response switch 1 is attachably and detachably provided on a right side of FIG. 1 of the main body 3 through a connection code 9, and a visual field dome 7 in a semispherical shape trough which stimuli are presented is provided in front of the jaw stand 5 and the forehead pad 6, that is, inside of the main body 3 of a back of the paper of FIG. 1. The visual field dome 7 is configured to have a structure in which the stimuli for perimetry (not shown) are projected at optional positions inside the visual field dome 7 through a well-known stimulus presentation device built in the main body 3.

Figure 2:
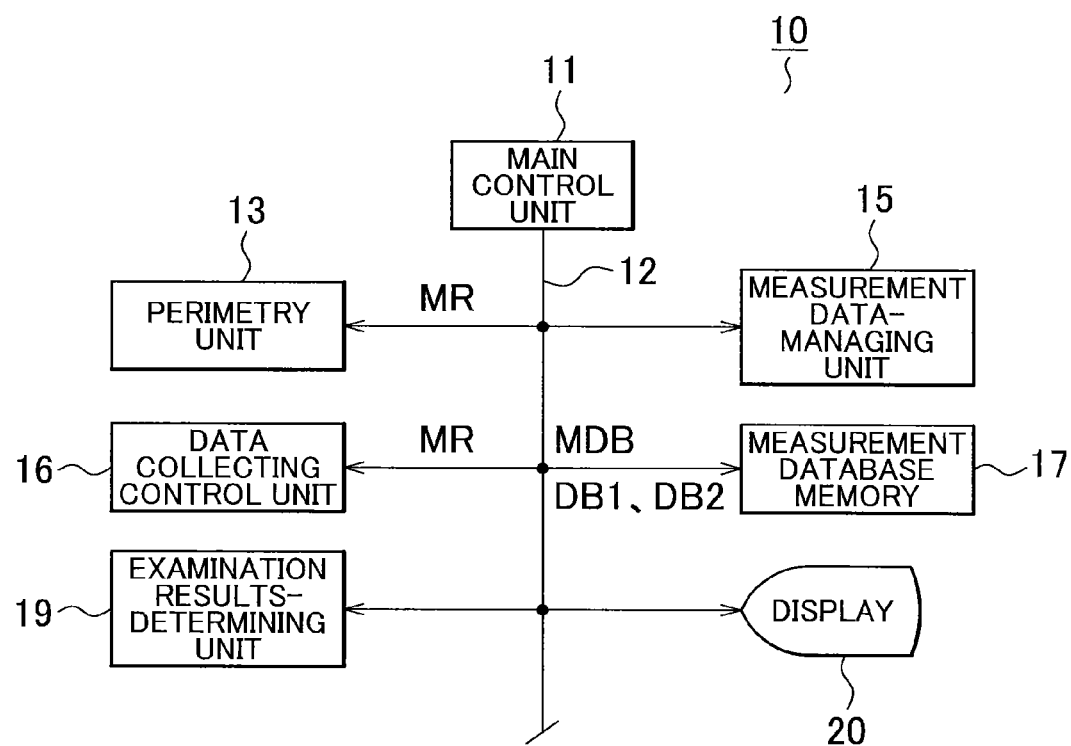
FIG. 2 is a control block diagram that shows an instance of control units of the perimeter of FIG. 1.

As shown in FIG. 2, a control unit 10 of the perimeter 2 is provided inside the main body 3, and the control unit 10 has a main control unit 11. And, a perimetry unit 13, a measurement data-managing unit 15, a data collecting control unit 16, a measurement database memory 17, an examination results-determining unit 19 and a display 20 are connected with the main control unit 11 via a bus line 12. A control block diagram as shown in FIG. 2 shows only parts pertinent to the invention, and does not show the other parts of the perimeter 2 having no relation to the invention.

In case of perimetry on test eyes with the above-mentioned structure of the perimeter 2, an examinee is invited to put his (her) jaw on the jaw stand 5 and contacts his (her) forehead with the forehead pad 6 so as to be pressed against such a pad such that the test eye of a front eye portion of the examinee is located at a predetermined perimetry position. When the perimeter 2 is instructed to start perimetry of the test eye through an operation portion, such as a keyboard (not shown) in the afore-mentioned state, the main control unit 11 of the control unit 10 instructs the perimetry unit 13 to measure the visual field of the test eye. Receiving such an instruction, the perimetry unit 13 sequently presents the stimulus (not shown) at proper positions inside the visual field dome 7 with a well-known method. When the examinee perceives the presented stimulus through the test eye, the examinee operates the response switch 1 and when not, no operation of the response switch 1 is done. The perimetry unit 13 measures the visual field of the test eye with a well-known method, relating the operation state of the response switch 1 and the stimulus position inside the visual field dome 7 at such a time with each other.

After obtaining a series of perimetry results regarding the test eye, measurement results MR is outputted from the perimetry unit 13 to the data collecting control unit 16. The data collecting control unit 16 judges how to store the obtained measurement results MR regarding the test eye in measurement database MDB stored in the measurement database memory 17. The measurement results MR of the test eye stores data, such as the subject's age, sex, race, visual acuity, refractive index, diagnosis, residence and date and time of examination as attribution data (attribution data for searching database) through an input by examiners via an input means (not shown). Besides, the measurement database memory 17 stores the perimetry results of many test eyes that have been measured through the perimeter 2 in the past as the measurement database MDB.

Figure 3:
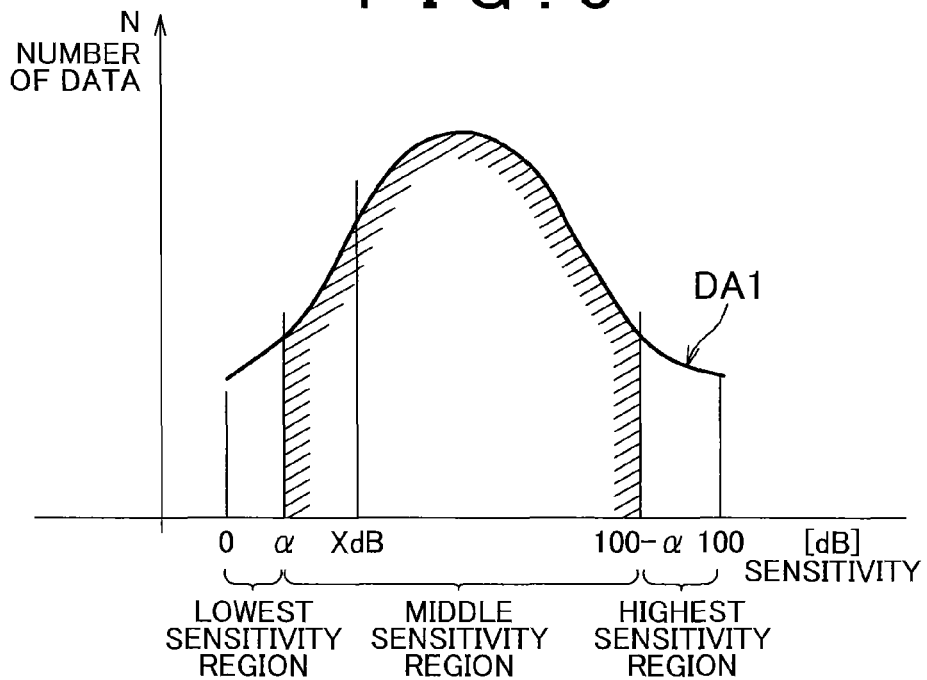
FIG. 3 is a view of an instance of a distribution of sensitivity measurement results of normal eyes in each examination point.

Database pertaining to normal eyes DB1 and database pertaining to eyes with glaucoma DB2 are stored in the measurement database MDB. The data collecting control unit 16 judges whether the obtained measurement results MR can be used as the measurement results of normal eyes from statistical and physiologic aspects. In order to do so, the data collecting control unit 16 reads the database pertaining to normal eyes of the measurement database MDB of the measurement database memory 17, and computes a distribution of sensitivity of the test eye of each perimetry point in the perimetry as sensitivity distribution data DA1 in normal eyes so as to store in a memory that is not shown (sensitivity distribution memory). Normally, in the sensitivity of the normal eyes, number of data (number of specimens of the test eyes comprising the database) N shows a tendency like normal distribution with respect to the sensitivity of the test eye (dB), as shown in FIG. 3. The data collecting control unit 16 judges that the measurement results MR is included in an intermediate sensitivity region that is a % from the lowest sensitivity or higher (that is, the lowest sensitivity region or higher) and 100-a % from the highest sensitivity or lower (that is, the highest sensitivity region or lower) provided that the lowest sensitivity of the specimens comprising the sensitivity distribution data DA1 stored in the memory is 0 (zero) and the highest sensitivity is 100. When being included, the measurement results MR is the measurement results of the normal eye and the measurement results MR is judged to be usable as the measurement results of the normal eye. The sensitivity distribution data DA1 in the normal eyes as shown in FIG. 3, that is, a graph of the distribution of the sensitivity of each perimetry point may be stored in the measurement database memory 17 or the like at a time of the manufacture of the perimeter 2 in advance as default data that collects the past measurement results obtained by the other perimeter. By doing so, it is possible to improve judgment precision of the perimeter 2 at the time of beginning of use of the perimeter 2 having small number of measurement data of the test eyes. A parameter a for setting the region may be optionally set in advance through input means, such as a keyboard, by the examiners or may be properly set by the data collecting control unit 16 according to a predetermined inspection program.

Figure 4:
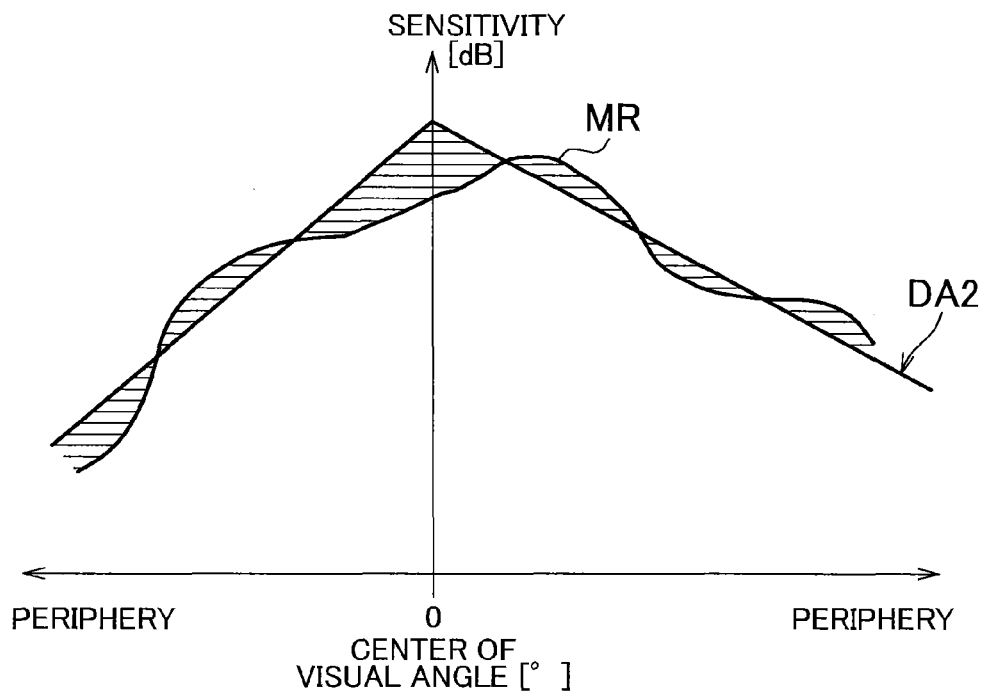
FIG. 4 is a view that shows an instance of a sensitivity distribution of measurement data with respect to a visual angle.

When the data collecting control unit 16 has statistically judged that the measurement results MR is usable as the measurement results of normal eyes, the data collecting control unit 16 judges as to whether the obtained measurement results MR is physiologically normal or not. In order to do so, the data collecting control unit 16 reads a visual angle-sensitivity distribution model DA2 as shown in FIG. 4 that shows the physiological sensitivity distribution with respect to the visual angle in the normal eye out of the measurement database memory 17. Such a visual angle-sensitivity distribution model in the normal eye may be stored in the measurement database memory 17 or the like in advance at the time of the manufacture of the perimeter 2 with a model well known as the physiological visual angle-sensitivity distribution as default data. After the perimeter 2 collects multiple measurement results MR regarding normal eyes as the database regarding the normal eyes DB1, such multiple measurement results MR may be read out of the database DB1 so as to compute for the data collecting control unit 16 the visual angle-sensitivity distribution model DA2 in the normal eye, and thus computed may be stored in a proper memory (model memory).

The data collecting control unit 16 compares the read (or computed) visual angle-sensitivity distribution model DA2 and the measurement results MR obtained this time with each other, and computes a divergence degree K of the measurement results MR with respect to the visual angle-sensitivity distribution model DA2 as an area enclosed by the measurement results MR and the visual angle-sensitivity distribution model DA2 as shown in a hatched portion of the figure. When the area is a predetermined value β or lower, the obtained measurement results MR is judged to be physiologically normal, that is, to be judged that the measurement results MR is usable as the measurement results of normal eyes. A predetermined value β may be optionally set in advance through input means, such as a keyboard, by the examiners or may be properly set by the data collecting control unit 16 according to a predetermined inspection program.

When the data collecting control unit 16 has judged that the measurement results MR is usable as the measurement results of normal eyes from statistical and physiologic aspects, the examiner is informed of the judgment results through the display 20, and at the same time, the measurement results MR is outputted to the measurement data-managing unit 15. The measurement data-managing unit 15 performs a processing of adding the measurement results MR to the database regarding normal eyes DB1 of the measurement database MDB stored in the measurement database memory 17. On this occasion, the data of the subject's age, sex, race, visual acuity, refractive index, diagnosis, residence, date and time of examination, is simultaneously stored as the attribution data for searching the database. By doing so, the database regarding normal eyes DB becomes more statistically reliable by addition of the measurement results MR. The judgment of the measurement results MR may be done from one of the statistical and physiologic aspects in order to do judgment processing easily without doing both.

When the data collecting control unit 16 has judged that the measurement results MR is not usable as the measurement results of normal eyes from statistical and physiologic aspects, the main control unit 11 gets the examination results-determining unit 19 to display the results on the display 20. The examiner suspects that the test eye may be glaucoma in view of the such judgment results that can not be adopted as the measurement results of normal eyes, reviews the measurement results MR and judges whether the test eye is glaucoma or not. When the examiner judged the measurement results MR is glaucoma, the examiner inputs a signal showing the measurement results MR is glaucoma through input means. Receiving such a signal, the main control unit 11 instructs the measurement data-managing unit 15 to add such measurement results MR to the database regarding the eyes with glaucoma DB2. The measurement data-managing unit 15 promptly performs a processing of adding the measurement results MR to the database regarding eyes with glaucoma DB2 of the measurement database MDB stored in the measurement database memory 17. In this case, the data, such as the subject's age, sex, race, visual acuity, refractive index, diagnosis, residence, date and time of examination, is simultaneously added thereto as the attribution data. By doing so, the database regarding glaucoma DB2 becomes more statistically reliable by addition of the measurement results MR.

Since the data, such as the subject's age, sex, race, visual acuity, refractive index, diagnosis, residence, date and time of examination, is simultaneously stored in the measurement database MDB comprised of the database regarding normal eyes DB1 and the database regarding eyes with glaucoma DB2 that are stored in the measurement database memory 17 as the attribution data, as mentioned above, it is possible for the examiner at a time of judgment of glaucoma of the measurement results MR to search the database DB1 or DB2 with age, sex, race, visual acuity, refractive index, diagnosis, residence, date and time of examination of the databases DB1 and DB2 as a parameter through the examination results-determining unit 19 via the input means so as to collect and display the data necessary for diagnosis of the glaucoma. Then, it is possible to extract various data effective for diagnosis, such as a difference of the visual field between normal eyes and myopic eyes and a difference of normal eye data due to a difference of the date and time of examination.

Furthermore, the measurement results MR judged to be usable as the measurement results of normal eyes through the data collecting control unit 16 is also outputted to the examination results-determining unit 19, and is presented to the examiner through the display 3. The examiner compares the presented measurement results MR and the data of the database regarding normal eyes DB1 of the measurement database MDB stored in the measurement database memory 17 that is searched through various parameters, such as age, sex, race, visual acuity, refractive index, diagnosis, residence, date and time of examination, so that it is possible to diagnose the state of the test eye in detail. At the time of the diagnosis of the measurement results MR, with which parameter the database DB1 has been searched for diagnosis may be recorded together with the diagnosis results.

The measurement database MDB adapted to an area where the perimeter 2 is installed is constructed by updating the measurement database MDB, thus adding the measurement results MR of the test eye obtained through the perimeter 2 in order, so that the diagnosis and the judgment fit for such an area are possible. When the measurement databases MDB from two or more perimeters 1 that are located at geographically different places are collected and analyzed, it is possible to do careful research on a regional difference of the perimetry results and a difference of symptom of glaucoma.

The examiner is possible to set the parameters or judgment rules to be used for the judgment in the control unit 10 of the perimeter 2 through input means, such as a keyboard, in advance. By doing so, it is possible to diagnose whether the measurement results MR shows the normal eyes or the eyes with glaucoma in such a way that previous measurement results is searched through various parameters, such as age, sex, race, visual acuity, refractive index, diagnosis, residence, date and time of examination, out of the database regarding normal eyes DB1 and the database regarding eyes with glaucoma DB2 stored in the measurement database memory 17 on the basis of a criterion set by the examiner himself, and the searched and the measurement results MR are compared with each other without judging for the examiner as to whether the measurement results MR is usable or not as the measurement result of normal eyes through the data collecting control unit 16 one by one.

The perimeter 2 may be configured in such a manner that the measurement database to be produced and stored in the measurement database memory 17 of the perimeter 2 is only the database regarding normal eyes DB1 (basic configuration), and the database regarding eyes with glaucoma DB2 may be produced and stored, depending on the needs such as diagnosis results, selectively through a software or by introducing an optional unit. With such a configuration, it is possible to rapidly process the measurement results, keeping the construction of the basic database regarding the normal eyes DB1.

Such a configuration may be possible that an examiner or a doctor reviews the measurement results MR, and manually instructs the data collecting control unit 16 to add the measurement results MR to the database regarding the normal eyes DB1 from the judgment of the examiner or the doctor through input means as well as the automatic addition processing through the data collecting control unit 16. By doing so, when a border region between a middle sensitivity region and a lowest sensitivity region and a border region between the middle sensitivity region and a highest sensitivity region as shown in FIG. 3, and an area enclosed by the measurement results MR and a visual angle-sensitivity distribution model DA2 as shown in FIG. 4 show a value near a border of a predetermined value β, it is possible to avoid such a situation that the measurement results is uniformly judged to be unusable as one of normal eyes.

In addition to the data, such as the subject's age, sex, race, visual acuity, refractive index, diagnosis, residence, date and time of examination, the attribution data to be stored in the database regarding glaucoma DB2 together with the measurement results MR is stage of disease of glaucoma to be judged from the examination results MR, such as an early stage, a middle stage and a last stage. The database regarding glaucoma DB2 can be made one according to a degree of a progress of a symptom by simultaneously storing the above-mentioned stages of disease of glaucoma, so that it is possible to properly judge the degree of the future progress of glaucoma.

Furthermore, the database regarding normal eyes DB1 may be stored in the measurement database memory 17, divided into the default database before storing the measurement results MR obtained through the perimeter 2, that is, the database storing data regarding multiple (two or more) measurement results of the test eyes that are generally considered to be normal eyes in advance in the measurement database memory 17 before the perimeter 2 is actually used for the measurement of the test eye, and the storage database storing multiple measurement results MR of the normal eyes obtained through the perimeter 2 by adding the measurement results MR obtained through the perimeter 2 to the default database in order. With such a configuration, it is possible to judge the measurement results MR with both default database and the storage database. Besides, the perimeter 2 may be configured to have such a structure that the previous measurement results MR are searched and extracted out of both databases, the default database and the storage database with the optional attribution data for searching database that is designated through the input means, such as a keyboard by the examiner as a parameter, and a new database having the common parameter is produced and constructed in the measurement database memory 17 (database producing means).

For example, the previous measurement results MR stored in the default database and the storage database are extracted out of both databases with the visual acuity as a parameter (for example, the eyesight judged to be myopia or so) to produce a new database. By doing so, it is possible to grasp how to change the sensitivity in the myopia with a passage of time and to apply at the time of the diagnosis of the test eye.

And, it may be configured that the measurement data-managing unit 15 stores the measurement database storing the measurement results MR in the measurement database memory of an external database unit through a communication line, such as the Internet, and the two or more perimeters 2 are free of access to the database unit as well as the storage of the measurement database in the measurement database memory 17 built in the perimeter 2 as shown in FIG. 2, so that it is possible to control and analyze the measurement results of the perimeters 2 located at various places on the database unit side, and to grasp local (geographic) characteristic and tendency of the measurement results MR. In such a case, the measurement data-managing unit 15 accesses the external measurement database and adds the measurement results MR in the respective perimeters 2 to the measurement database.

EXPLANATION OF REFERENCE NUMBERS

2 . . . perimeter
13 . . . visual field measuring means (perimetry unit)
15 . . . database managing means (measurement data-managing unit)
16 . . . normal eyes data judging means sensitivity distribution computing means distribution model computing means (data collecting control unit)
19 . . . judgment results output means (examination results-determining unit)
17 . . . measurement database memory
20 . . . display
MR . . . measurement results
DA1 . . . sensitivity distribution data
DA2 . . . visual angle-sensitivity distribution model
DB1 . . . database regarding normal eyes
DB2 . . . database regarding eyes with glaucoma
MDB . . . measurement database

The invention claimed is:

1. A perimeter having perimetry means that measures a visual field of a test eye and outputs its results as measurement results, comprising:
   a measurement database memory that stores the measurement results regarding normal eyes from two or more measurement results of previous visual field measurements as a database regarding normal eyes;
   normal eyes data judging means that judges as to whether the measurement results of the test eye is usable as the measurement results of normal eyes;
   database control means that when the normal eyes data judging means judged the measurement results to be usable as the measurement results of normal eyes, adds the measurement results to the database regarding normal eyes together with attribution data for searching database.

2. The perimeter according to claim 1, wherein the measurement database memory stores the database regarding eyes with glaucoma in addition to the database regarding normal eyes, and stores two or more measurement results of the previous visual field measurements as a measurement database, differentiating the database regarding normal eyes and the database regarding eyes with glaucoma from each other.

3. The perimeter according to claim 1, further comprising a sensitivity distribution memory that stores sensitivity distribution data showing sensitivity distribution of the test eyes of each measurement point in the visual filed measurement on the normal eyes, wherein the normal eyes data judging means judges as to whether the measurement results is usable as the measurement results of normal eyes by such a judgment as to whether the measurement results is included in the middle sensitivity region of the sensitivity distribution data between the lowest sensitivity region and the highest sensitivity region, and when it is included in the middle sensitivity region, the measurement results is judged to be usable as one of normal eyes.

4. The perimeter according to claim 1, further comprising a model memory that stores visual angle-sensitivity distribution model showing a sensitivity distribution in normal eyes with respect to the visual angle, wherein the normal eyes data judging means judges as to whether the measurement results is usable as the measurement results of normal eyes by a judgment as to whether a divergence degree of the measurement results with respect to the visual angle-sensitivity distribution model is a predetermined value or lower, and judges the measurement results to be usable as the measurement results of normal eyes when such a divergence degree is a predetermined value or lower.

5. The perimeter according to claim 3, further comprising sensitivity distribution computing means that reads the database regarding normal eyes out of the measurement database memory, computes sensitivity distribution data that shows the distribution of the sensitivity of the test eyes of each measurement point, and stores the computed in the sensitivity distribution memory.

6. The perimeter according to claim 4, further comprising distribution model computing means that reads the database regarding normal eyes out of the measurement database memory so as to compute the visual angle-sensitivity distribution model, and stores the computed in the model memory.

7. The perimeter according to claim 1, further comprising a sensitivity distribution memory that stores sensitivity distribution data showing a sensitivity distribution of the test eyes of each measurement point in the visual field measurement on the normal eyes, and a model memory that stores a visual angle-sensitivity distribution model showing the sensitivity distribution in the normal eyes with respect to the visual angle, wherein the normal eyes data judging means judges as to whether the measurement results is usable as the measurement results of normal eyes by 1) a judgment as to whether the measurement results is included in a middle sensitivity region of the sensitivity distribution data between a lowest sensitivity region and a highest sensitivity region and 2) a judgment as to whether a divergence degree of the measurement results with respect to the visual angle-sensitivity distribution model is a predetermined value or lower, and judges the measurement results to be usable as the measurement results of normal eyes when the measurement results is included in the middle sensitivity region and the divergence degree of the measurement results with respect to the visual angle-sensitivity distribution model is a predetermined value or lower.

8. The perimeter according to claim 7, further comprising sensitivity distribution computing means that reads the database regarding normal eyes out of the measurement database memory so as to compute sensitivity distribution data showing the distribution of the sensitivity of the test eyes of each measurement point, and stores the computed in the sensitivity distribution memory, and distribution model computing means that reads the database regarding normal eyes out of the measurement database memory so as to compute the visual angle-sensitivity distribution model, and stores the computed in the model memory.

9. The perimeter according to claim 2, further comprising judgment result output means that displays the measurement results on a display when the normal eyes data judging means judged the measurement results to be unusable as the measurement results of normal eyes, wherein the database managing means adds the measurement results to the database regarding eyes with glaucoma together with the attribution data for searching database when a signal that shows the measurement results is glaucoma is inputted through input means.

10. A perimeter having perimetry means that measures a visual field of a test eye and outputs its results as measurement results, comprising:
a data storing means that stores the measurement results regarding normal eyes from two or more measurement results of previous visual field measurements in a measurement database memory provided at an outside of the perimeter as a database regarding normal eyes;
normal eyes data judging means that judges as to whether the measurement results of the test eye is usable as the measurement results of normal eyes; and
database control means that when the normal eyes data judging means judged the measurement results to be usable as the measurement results of normal eyes, adds the measurement results to the database regarding normal eyes together with attribution data for searching database.

11. The perimeter according to claim 1, wherein the database regarding normal eyes is stored in the measurement database memory, divided into 1) a default database and 2) a storage database, and 1) the default database storing the two or more measurement results of the test eyes that are considered to be normal eyes in the measurement database memory in advance as a database before the perimeter is actually used for the measurement of the test eye, and 2) the storage database storing multiple measurement results of the normal eyes measured with the perimeter by adding the measurement results measured by the perimeter to the default database in order.

12. The perimeter according to claim 11, further comprising database producing means that searches and extracts the measurement results out of the default database and the storage database with the attribution data for searching the database as a parameter so as to produce and construct a new database.

13. The perimeter according to claim 10, wherein the database regarding normal eyes is stored in the measurement database memory, divided into 1) a default database and 2) a storage database, and 1) the default database storing the two or more measurement results of the test eyes that are considered to be normal eyes in the measurement database memory in advance as a database before the perimeter is actually used for the measurement of the test eye, and 2) the storage database storing multiple measurement results of the normal eyes measured with the perimeter by adding the measurement results measured by the perimeter to the default database in order.

* * * * *